United States Patent [19]

Yagihara et al.

[11] 4,296,200
[45] Oct. 20, 1981

[54] SILVER HALIDE PHOTOGRAPHIC LIGHT-SENSITIVE MATERIAL

[75] Inventors: Morio Yagihara; Yukio Yokota, both of Minami-ashigara, Japan

[73] Assignee: Fuji Photo Film Co., Ltd., Minami-ashigara, Japan

[21] Appl. No.: 177,337

[22] Filed: Aug. 12, 1980

[30] Foreign Application Priority Data

Aug. 13, 1979 [JP] Japan ................................ 54-102963

[51] Int. Cl.³ .............................................. G03C 1/40
[52] U.S. Cl. .................................... 430/551; 430/385; 430/553; 430/558
[58] Field of Search ................ 430/385, 553, 558, 551

[56] References Cited

U.S. PATENT DOCUMENTS 3,476,563 11/1969 Loria .................................... 430/553
3,580,721 5/1971 Iwama et al. ........................ 430/553
4,124,396 11/1978 Osborn ................................ 430/553

Primary Examiner—J. Travis Brown
Attorney, Agent, or Firm—Sughrue, Mion, Zinn, Macpeak and Seas

[57] ABSTRACT

A silver halide photographic light-sensitive material containing a colorless photographic cyan color forming coupler having, in a position for coupling with an oxidation product of an aromatic primary amine developing agent, a coupling-off group represented by the formula (I):

$$-O-R-S-R_1 \quad (I)$$

wherein R represents a substituted alkylene group or an unsubstituted or substituted alkenylene group, and said alkylene group or alkenylene group may be straight or branched chain; and $R_1$ represents a substituted or unsubstituted alkyl group, an alkenyl group, an aralkyl group, an aralkenyl group, a cycloalkyl group or a heterocyclic group and said alkyl group, alkenyl group, aralkyl group and aralkenyl group may be straight or branched chain; and said heterocyclic group being connected with a thio group at the position of a carbon atom of the heterocyclic group.

18 Claims, No Drawings

SILVER HALIDE PHOTOGRAPHIC LIGHT-SENSITIVE MATERIAL

BACKGROUND OF THE INVENTION

1. Field of the Invention

This invention relates to a photographic color coupler and, more particularly, to a novel 2-equivalent cyan coupler, color photographic light-sensitive material containing such a coupler, and to image-forming processes using such couplers.

2. Description of the Prior Art

It is well known that when an imagewise exposed silver halide photographic light-sensitive material is subjected to color development processing, an oxidation product of the aromatic primary amine developing agent reacts with a dye-forming coupler to form a color image.

Usually, a color-reproducing process based on subtractive color photography is relied upon forming cyan, magenta, and yellow color images, the colors of which are in complementary relationship with red, green, and blue, respectively. For example, phenolic derivatives or naphtholic derivatives are used as couplers for forming cyan color images.

In color photography, color-forming couplers are added to a developer or incorporated in a light-sensitive photographic emulsion layer or other color image-forming layer and, when reacted with an oxidation product of a color-developing agent formed upon development, they form non-diffusing dyes. The reaction between the coupler and the color-developing agent proceeds at the active site of the coupler. Couplers having a hydrogen atom at this active site are 4-equivalent couplers which theoretically require 4 moles of silver halide with a developing center (exposed silver halide) as an oxidizing agent for forming one mole of a dye. On the other hand, couplers having at the active site a group capable of being eliminated as an anion are 2-equivalent couplers which require only two moles of silver halide with a developing center and, therefore, they generally permit a reduction in the amount of silver halide incorporated in a light-sensitive layer and in the thickness of the film, thus enabling shortening of the time for processing light-sensitive materials and improving sharpness of color images to be formed.

Such coupling-off (eliminatable) groups are known. For example, U.S. Pat. No. 3,737,316 describes a sulfonamido group, U.S. Pat. No. 3,749,735 describes an imido group, U.S. Pat. No. 3,622,328 describes a sulfonyl group, U.S. Pat. No. 3,476,563 describes an aryloxy group, U.S. Pat. No. 3,311,476 describes an acyloxy group, and U.S. Pat. No. 3,214,437 describes a thiocyano group. Furthermore, U.S. Pat. No. 4,032,345 describes an isocyanato group, U.S. Pat. No. 4,046,573 describes a sulfonyloxy group, Japanese patent application (OPI) No. 51939/77 describes a thiocarbonyloxy group, Japanese patent application (OPI) Nos. 39126/78 and 39745/78 describe an aralkenylcarbonyloxy group, Japanese patent application (OPI) No. 45524/78 describes an S-substituted monothiocarbonyloxy group, Japanese patent application (OPI) No. 47827/78 describes a propioloyloxy group, U.S. Pat. No. 4,072,525 describes the group

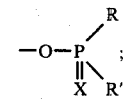

and U.S. Pat. Nos. 3,227,551, 4,052,212, 4,134,766 and 4,146,396, Japanese patent application (OPI) Nos. 120334/75, and 105226/78, French Pat. No. 2,321,715 and German patent application (OLS) No. 2,805,707 describe substituted alkoxy groups.

Proper selection of such coupling-off groups, for example, selection of a group having a diffusible dye moiety, permits the use of the couplers in a diffusion transfer process wherein images of diffusible dyes are formed in an image-receiving layer. Such couplers are called diffusible dye-releasing (DDR) couplers and are described in, for example, U.S. Pat. Nos. 3,227,550, 3,765,886, U.S. Defensive Publication T 900,029, British Pat. No. 1,330,524, etc. Some colored 2-equivalent couplers exhibit a masking effect for color correction of a dye image, and such couplers are called colored couplers described in, for example, British Pat. No. 1,501,743.

Furthermore, 2-equivalent couplers releasing a compound having a development suppressing effect, which are referred to as development inhibitor releasing (DIR) couplers, are also known. Since these couplers can suppress or inhibit development in proportion to the amount of the developed silver, these couplers are quite effective in reducing the image-forming particle size (thus improving image graininess), gradation control, and improving color reproduction characteristics. These couplers can also be used in a diffusion transfer process to affect a layer adjacent to the layer in which they are present. Examples of these couplers are described in U.S. Pat. Nos. 3,227,554, and 3,933,500.

Since a 2-equivalent couplers generally have certain advantages and a wider range of applications as compared with a 4-equivalent couplers, the photographic industry tends to use this type of coupler more frequently.

However, most known 2-equivalent cyan color forming couplers have certain disadvantages, such as that the coupling reactivity is insufficient, that color fog is formed, that the dispersibility thereof is poor (which causes difficulties during coating), that the compound per se is unstable and cannot be stored for a long time, and that the storage stability of the resulting color image formed by color development is poor. Thus improvements to overcome these disadvantages have been desired.

SUMMARY OF THE INVENTION

An object of the present invention is, therefore, to provide novel 2-equivalent cyan forming couplers which overcome the defects described above and which have an excellent color forming and dispersion properties.

Another object of the present invention is to provide novel 2-equivalent cyan forming couplers having high coupling speed.

Still another object of the present invention is to provide a process for forming a cyan color image by developing a silver halide emulsion in the presence of a novel 2-equivalent coupler.

A further object of the present invention is to provide a silver halide color photographic light-sensitive material containing a novel 2-equivalent coupler and a method of photographic processing or a method for forming images using that light-sensitive material.

As a result of various investigations, it has now been discovered that the above-described objects can effectively be attained using a colorless photographic cyan color forming coupler having at the coupling position at which the coupler reacts with the oxidation product of an aromatic primary amine developing agent, a coupling-off group represented by the formula (I):

wherein R represents a substituted alkylene group or an unsubstituted or substituted alkenylene group and said alkylene and alkenylene group may be straight or branched chain; and $R_1$ represents a substituted or unsubstituted alkyl group, an alkenyl group, an aralkyl group, an aralkenyl group, a cycloalkyl group or a heterocyclic group; and said alkyl, alkenyl, aralkyl and aralkenyl groups may be straight or branched chain; and said heterocyclic group being connected with a thio group at the position of a carbon atom of the heterocyclic group.

DETAILED DESCRIPTION OF THE INVENTION

The group represented by general formula (I) above is split off when a cyan dye is formed by the coupling reaction.

The term "colorless" couplers as used herein means those couplers whose molecular extinction coefficient at the absorption maximum wavelength thereof does not exceed 5,000 within the visible light region.

Preferred couplers of this invention are couplers represented by the formula (IA):

where A represents a cyan color forming coupler residue having a naphtholic or phenolic nucleus; R represents a substituted alkylene group containing from 1 to 18 carbon atoms (examples of the alkylene group including, for example, a methylene group, a dimethylene group, a trimethylene group, a 2-methyldimethylene group, a 2-methyltrimethylene group, a tetramethylene group, an octamethylene group, a dodecylmethylene group, etc.) or an unsubstituted or substituted alkenylene group having from 2 to 18 carbon atoms (for example, a 2-butenylene group, etc.). These alkylene groups and alkenylene groups may be straight or branched chain. R preferably represents a substituted alkylene group from 1 to 4 carbon atoms.

The substituents for the alkylene and alkenylene group can include an aryl group (for example, a phenyl group, a naphthyl group, etc.), a nitro group, a hydroxy group, a cyano group, a sulfor group, an alkoxy group (for example, a methoxy group, an ethoxy group, a methoxyethoxy group, etc.), an aryloxy group (for example, a phenoxy group, etc.), an acyloxy group (for example, an acetoxy group, a benzoyloxy group, etc.), an acylamino group (for example, an acetylamino group, a benzoylamino group, etc.), a sulfonamido group (for example, a methanesulfonamido group, a methanesulfonamido group, a phenylsulfonamido group, etc.), a sulfamoyl group (for example, a methylsulfamoyl group, a phenylsulfamoyl group, etc.), a halogen atom (for example, a fluorine atom,, a chlorine atom, a bromine atom, etc.), a carboxy group, a carbamoyl group (for example, a methylcarbamoyl group, a phenylcarbamoyl group, etc.), an alkoxycarbonyl group (for example, a methoxycarbonyl group, an ethoxycarbonyl group, etc.), an acyl group (for example, an acetyl group, a benzoyl group, etc.), a sulfonyl group (for example, a methylsulfonyl group, a phenylsulfonyl group, etc.), a sulfinyl group (for example, a methylsulfinyl group, a phenylsulfinyl group, etc.), a heterocyclic group (for example, a morpholino group, a pyrazolyl group, a triazolyl group, etc.), an amino group (for example, an unsubstituted amino group, an ethylamino group, etc.), or a thioether group represented by the formula $-S-R_1$. When there are two or more substituents, the substituent groups may be the same or different.

$R_1$ represents an alkyl group containing 1 to 18 carbon atoms (for example, a methyl group, an ethyl group, an n-propyl group, an iso-propyl group, an n-butyl group, an iso-butyl group, a tert-butyl group, an n-hexyl group, an n-octyl group, an n-dodecyl group, an n-octadecyl group, etc.), an alkenyl group containing from 2 to 18 carbon atoms (for example, a propenyl group, a butenyl group, an octenyl group, etc.), an aralkyl group containing from 7 to 18 carbon atoms (for example, a benzyl group, a phenylethyl group, etc.), an aralkenyl group containing from 8 to 18 carbon atoms (for example, a phenylpropenyl group, etc.), a cycloalkyl group (for example, a cyclopentyl group, a cyclohexyl group, a methylcyclohexyl group, a cycloheptyl group, etc.) or a 5-membered or 6-membered heterocyclic group in which the hetero ring may contain one nitrogen atom and further an oxygen atom, a sulfur atom and/or a nitrogen atom (for example, an imidazolyl group, a pyrazolyl group, a triazolyl group, a tetrazolyl group, a thiazolyl group, a piperazyl group, etc.). Each of the alkyl group, alkenyl group, aralkyl group, aralkenyl group, cycloalkyl group, and heterocyclic group represented by $R_1$ may be substituted with a substituent, for example, a halogen atom (fluorine, chlorine, or bromine), a cyano group, a hydroxy group, an alkoxy group (for example, a methoxy group, an ethoxy group, a propyloxy group, a butoxy group, an octyloxy group, etc.), an aryloxy group (for example, a phenoxy group, etc.) an acyloxy group (for example, an acetyloxy group, a propionoyloxy group, a butyroyloxy group, a benzoyloxy group, etc.), an acylamino group (for example, a formamino group, an acetylamino group, a propionoylamino group, a benzoylamino group, etc.), a sulfonamido group (for example, a methylsulfonamido group, an octylsulfonamido group, a benzenesulfonamido group, etc.), a sulfamoyl group (for example, an unsubstituted sulfamoyl group, a methylsulfamoyl group, an ethylsulfamoyl group, a propylsulfamoyl group, a phenylsulfamoyl group, etc.), a sulfonyl group (for example, a methylsulfonyl group, an ethylsulfonyl group, an octylsulfonyl group, a benzenesulfonyl group, etc.), a carboxy group, a sulfo group, a nitro group, an arylthio group (for example, a phenylthio group, etc.), an alkylthio group (for example, a methylthio group, an ethylthio group, etc.), a carbamoyl group (for example, an ethylcarbamoyl group, a phenylcarbamoyl group, etc.), an alkoxycarbonyl group (for example, a methoxycarbonyl group, an ethoxycarbonyl group, etc.), a sulfinyl group (for example, a methylsulfinyl group, a phenylsulfinyl group, etc.), a heterocyclic group (for example, a pyrazolyl group, a triazolyl group, etc.), and the like. These substituents may be further substituted with these substituents. Two or more substituents may be present simultaneously, and such substituents may be the same or different.

Furthermore, the alkyl group, the alkenyl group, the aralkyl group, the aralkenyl group represented by $R_1$ may be straight or branched chain. Said heterocyclic group being connected with a thio group at the position of a carbon atom of the heterocyclic group.

The letter m represents a positive integer.

Preferred groups for $R_1$ in the general formula (IA) are a substituted or unsubstituted alkyl group, an alkenyl group, a cycloalkyl group and a 5-membered or 6-membered heterocyclic group.

Of the compounds represented by the general formula (IA), compounds wherein $R_1$ represents a straight chain or branched chain alkyl group substituted with a carboxy group, a hydroxy group or a sulfo group and R represents a straight chain or branched chain alkylene group substituted with an alkylthio group represented by the formula $-S-R_{11}$, wherein $R_{11}$ has the same meaning as $R_1$, or a hydroxy group are particularly preferred.

Also, the carboxy group and the sulfo group may form a salt with an alkali metal atom (for example, lithium, sodium, potassium, etc.), an alkaline earth metal atom (for example, calcium, barium, etc.) or an ammonium (for example, triethylammonium, pyridinium, etc.).

In the aforesaid general formula (IA), the cyan coupler residue is a residue of a cyan color forming coupler from which a hydrogen atom or a coupling-off group at the active site of a cyan coupler is removed and, where a plural number of active sites exist in the same molecule, the coupling-off groups introduced at the respective active sites may be the same or different, or a hydrogen atom may be introduced. Preferably, however, all active sites have the coupling-off group of the present invention.

Furthermore, m preferably represents 1 or 2, in the case of using a polymeric cyan coupler, n may be 3 or more.

Of the couplers of the present invention, particularly useful are those represented by the following general formula (IIA) or (IIB):

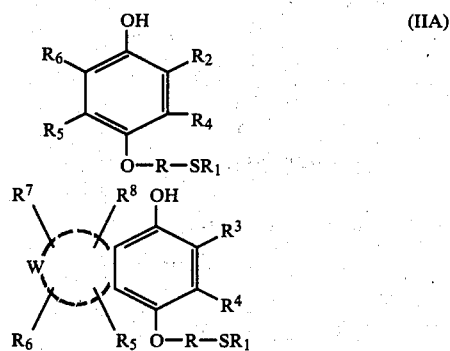

In the above general formulae, R and $R_1$ each has the same meaning as defined for R and $R_1$ in the general formula (I) above.

$R_2$ represents hydrogen, an aliphatic group containing up to 30 carbon atoms (for example, an alkyl group such as a methyl group, an isopropyl group, a pentadecyl group, an eicosyl group, or the like), an alkoxy group containing up to 30 carbon atoms (for example, a methoxy group, an isopropoxy group, a pentadecyloxy group, an eicosyloxy group, or the like), an aryloxy group (for example, a phenoxy group, a p-tert-butylphenoxy group, or the like), an acylamido group, a sulfonamido group, a phosphoric acid amido group, a ureido group represented by the following formulae (III) to (VI), or a carbamoyl group represented by the following formula (VII) or (VIII):

$$-NH-CO-B \qquad (III)$$

$$-NH-SO_2-B \qquad (IV)$$

$$-NHCONH-B \qquad (VI)$$

$$-CONH-B \qquad (VII)$$

wherein B and B' may be the same or different and each represents an aliphatic group containing from 1 to 32 carbon atoms, and preferably a straight or branched alkyl group containing from 1 to 20 carbon atoms, a cyclic alkyl group (for example, a cyclopropyl group, a cyclohexyl group, a norbornyl group, or the like), or an aryl group (for example, a phenyl group, a naphthyl group, or the like). The above-described alkyl group and aryl group may be substituted by a halogen atom (for example, fluorine, chlorine, or the like), a nitro group, a cyano group, a hydroxy group, a carboxy group, an amino group (for example, an amino group, an alkylamino group, a dialkylamino group, an anilino group, an N-alkylanilino group, or the like), an alkyl group (for example, those described hereinbefore), an aryl group (for example, a phenyl group, an acetylaminophenyl group, or the like), an alkoxycarbonyl group (for example, a tetradecyloxycarbonyl group, or the like), an acyloxycarbonyl group, an amido group (for example, an acetamido group, a methane-sulfonamido group, or the like), an imido group (for example, a succinimido group, or the like), a carbamoyl group (for example, an N,N-dihexylcarbamoyl group, or the like), a sulfamoyl group (for example, an N,N-diethylsulfamoyl group, or the like), an alkoxy group (for example, an ethoxy group, a tetradecyloxy group, an octadecyloxy group, or the like), an aryloxy group (for example, a phenoxy group, a p-tert-butylphenoxy group, a 2,4-di-amylphenoxy group, a 4-hydroxy-3-tert-butylphenoxy group, or the like), etc.

D and D' each represents B described above or one of $-OB$, $-NHB$, or $-NB_2$.

$R_3$ is selected from among a hydrogen atom, an aliphatic group containing up to 30 carbon atoms (particularly, an alkyl group containing from 1 to 20 carbon atoms), and a carbamoyl group represented by the formula (VII) or (VIII).

$R_4$, $R_5$, $R_6$, $R_7$ and $R_8$ each represents hydrogen, a halogen atom, an alkyl group, an aryl group, an alkoxy group, an alkylthio group, a heterocyclic group, an amino group, a carbonamido group, a sulfonamido group, a sulfamyl group, or a carbamyl group. For example, $R_4$ can represent one of the following groups: hydrogen, a halogen atom (for example, a chlorine atom, a bromine atom, or the like), a primary, secondary, or tertiary alkyl group containing from 1 to 22 carbon atoms (for example, a methyl group, a propyl group, an isopropyl group, an n-butyl group, a sec-butyl group, a tert-butyl group, a hexyl group, a dodecyl group, a 2-chlorobutyl group, a 2-hydroxyethyl group, a 2-phenylethyl group, a 2-(2,4,6-trichlorophenyl)ethyl group, a 2-aminoethyl group, or the like), an alkylthio group (for example, a hexadecylthio group, or the like), an aryl group (for example, a phenyl group, a 4-methylphenyl group, a 2,4,6-trichlorophenyl group, a 3,5-dibromophenyl group, a 4-trifluoromethylphenyl group, a 2-trifluoromethylphenyl group, a 3-trifluoromethylphenyl group, a naphthyl group, a 2-chloronaphthyl group, a 3-ethylnaphthyl group, or the like), a heterocyclic group (for example, a benzofuranyl group, a furanyl group, a thiazolyl group, a benzothiazolyl group, a naphthothiazolyl group, an oxazolyl group, a benzoxazolyl group, a naphthoxazolyl group, a pyridyl group, a quinolinyl group, or the like), an amino group (for example, an amino group, a methylamino group, a diethylamino group, a dodecylamino group, a phenylamino group, a tolylamino group, a 4-(3-sulfobenzamido)anilino group, a 4-cyanophenylamino group, a 2-trifluoromethylphenylamino group, a benzothiazolamino group, or the like), a carbonamido group [for example, an alkylcarbonamido group (e.g., an ethylcarbonamido group, a decylcarbonamido group, a phenylethylcarbonamido group, etc.); an arylcarbonamido group (e.g., a phenyl carbonamido group, a 2,4,6-trichlorophenylcarbonamido group, a 4-methylphenylcarbonamido group, a 2-ethoxyphenylcarbonamido group, a 3-[α-(2,4-di-tert-amylphenoxy)acetamido]benzamido group, a naphthylcarbonamido group, etc.); a heterocyclic ring carbonamido group (e.g., a thiazolylcarbonamido group, a benzothiazolylcarbonamido group, a naphthothiazolylcarbonamido group, an oxazolylcarbonamido group, a benzoxazolylcarbonamido group, an imidazolylcarbonamido group, a benzimidazolylcarbonamido group, etc.), or the like], a sulfonamido group [for example, an alkylsulfonamido group (e.g., a butylsulfonamido group, a dodecylsulfonamido group, a phenylethylsulfonamido group, etc.); an arylsulfonamido group (e.g., a phenylsulfonamido group, a 2,4,6-trichlorophenylsulfonamido group, a 2-methoxyphenylsulfonamido group, a 3-carboxyphenylsulfonamido group, a naphthylsulfonamido group, etc.); a heterocyclic ring sulfonamido group (e.g., a thiazolylsulfonamido group, a benzothiazolylsulfonamido group, an imidazolylsulfonamido group, a benzimidazolylsulfonamido group, a pyridylsulfonamido group, etc.), or the like], a sulfamyl group [for example, an alkylsulfamyl group (e.g., a propylsulfamyl group, an octylsulfamyl group, a pentadecylsulfamyl group, an octadecylsulfamyl group, etc.); an arylsulfamyl group (e.g., a phenylsulfamyl group, a 2,4,6-trichlorophenylsulfamyl group, a 2-methoxyphenylsulfamyl group, a naphthylsulfamyl group, etc.); a heterocyclic ring sulfamyl group (e.g., a thiazolylsulfamyl group, a benzothiazolylsulfamyl group, an oxazolylsulfamyl group, a benzimidazolylsulfamyl group, a pyridylsulfamyl group, etc.); or the like], and a carbamyl group [for example, an alkylcarbamyl group (e.g., an ethylcarbamyl group, an octylcarbamyl group, a pentadecylcarbamyl group, an octadecylcarbamyl group, etc.); an arylcarbamyl group (e.g., a phenylcarbamyl group, a 2,4,6-trichlorophenylcarbamyl group, etc.); a heterocyclic ring carbamyl group (e.g., a thiazolylcarbamyl group, a benzothiazolylcarbamyl group, an oxazolylcarbamyl group, an imidazolylcarbamyl group, a benzimidazolylcarbamyl group, etc.); or the like]. As the examples of $R_5$, $R_6$, $R_7$ and $R_8$, those illustrated for $R_4$ can be used. W represents non-metallic atoms necessary to form 5- and/or 6-membered ring such as a benzene ring, a cyclohexane ring, a cyclopentene ring, a thiazole ring, an oxazole ring, an imidazole ring, a pyridine ring, a pyrrole ring, etc., with a benzene ring being preferred.

The colorless 2-equivalent cyan color-forming couplers of the present invention provide extremely high sensitivity, high gradation, and high maximum density. Thus, they permit a reduction in the amount of silver halide incorporated in the photographic emulsion, and are suitable for not only ordinary processing but rapid processing as well. Also, the couplers have superior dispersion property due to the thioether group present in the coupling-off group. Further, they do not cause fogging, color stain, etc. of a light-sensitive layer. Dyes obtained from such cyan couplers show excellent durability against light, heat, and humidity and show good light absorption characteristics in that they do not have unnecessary absorptions and that they show sharp absorptions; additionally, such dyes are useful for forming images in a so-called conventional system.

Typical examples of the specific coupling-off groups of the two-equivalent cyan couplers according to the present invention will be illustrated below.

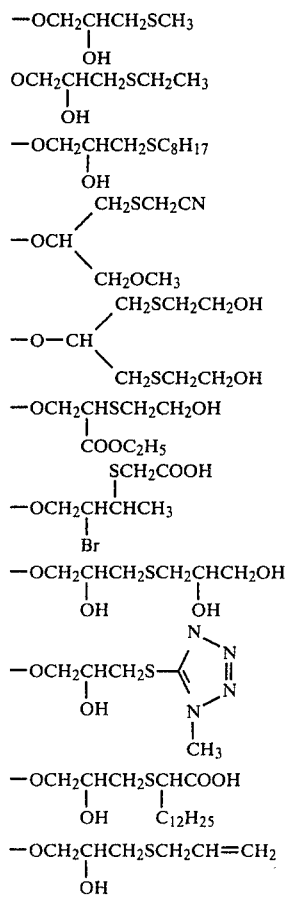

-continued

—OCH$_2$CHSCH$_2$CH$_2$OH
　　|
　　COOH

—OCH$_2$CHCH$_2$SCH$_2$COOH
　　|
　　OH

—OCH$_2$CHCH$_2$SCH$_2$COOH
　　|
　　Cl

—OCH$_2$CHCH$_2$SCH$_2$COOH
　　|
　　NHSO$_2$CH$_3$

—OCH$_2$CHCH$_2$SCH$_2$COOH
　　|
　　O—⟨C$_6$H$_4$⟩—COOH

—OCH$_2$CHCH$_2$SCH$_2$COOH
　　|
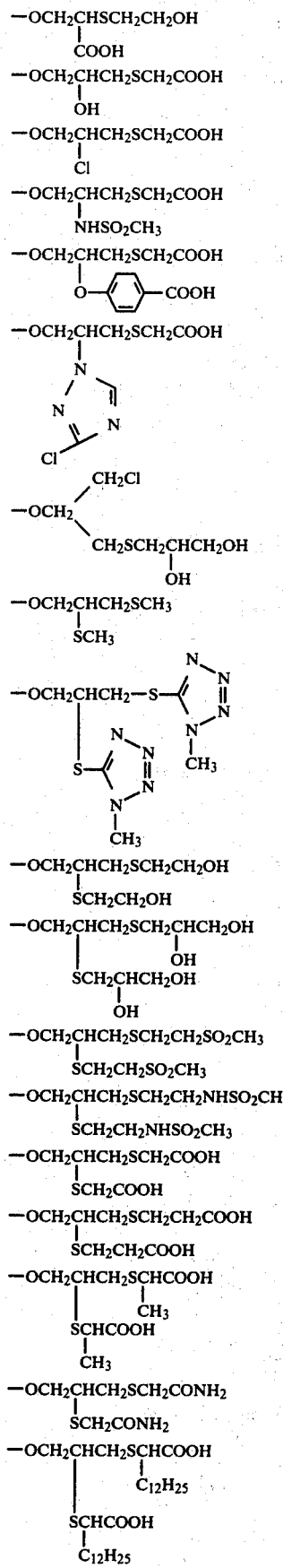

—OCH$_2$CH(CH$_2$Cl)—CH$_2$SCH$_2$CHCH$_2$OH
　　　　　　　　　　　　　　　　　|
　　　　　　　　　　　　　　　　　OH

—OCH$_2$CHCH$_2$SCH$_3$
　　|
　　SCH$_3$

—OCH$_2$CHCH$_2$—S—⟨tetrazole-N-CH$_3$⟩
　　|
　　S—⟨tetrazole-N-CH$_3$⟩

—OCH$_2$CHCH$_2$SCH$_2$CH$_2$OH
　　|
　　SCH$_2$CH$_2$OH

—OCH$_2$CHCH$_2$SCH$_2$CHCH$_2$OH
　　|　　　　　　　|
　　　　　　　　　OH
　　SCH$_2$CHCH$_2$OH
　　　　　|
　　　　　OH

—OCH$_2$CHCH$_2$SCH$_2$CH$_2$SO$_2$CH$_3$
　　|
　　SCH$_2$CH$_2$SO$_2$CH$_3$

—OCH$_2$CHCH$_2$SCH$_2$CH$_2$NHSO$_2$CH$_3$
　　|
　　SCH$_2$CH$_2$NHSO$_2$CH$_3$

—OCH$_2$CHCH$_2$SCH$_2$COOH
　　|
　　SCH$_2$COOH

—OCH$_2$CHCH$_2$SCH$_2$CH$_2$COOH
　　|
　　SCH$_2$CH$_2$COOH

—OCH$_2$CHCH$_2$SCHCOOH
　　|　　　　　　　|
　　　　　　　　　CH$_3$
　　SCHCOOH
　　　|
　　　CH$_3$

—OCH$_2$CHCH$_2$SCH$_2$CONH$_2$
　　|
　　SCH$_2$CONH$_2$

—OCH$_2$CHCH$_2$SCHCOOH
　　|　　　　　　　|
　　　　　　　　　C$_{12}$H$_{25}$
　　SCHCOOH
　　　|
　　　C$_{12}$H$_{25}$

-continued

—OCH$_2$CHCH$_2$SCH$_2$CH$_2$SO$_3$H
　　|
　　SCH$_2$CH$_2$SO$_3$H

—OCH$_2$CHCH$_2$SCH$_2$COONa
　　|
　　SCH$_2$COONa

—OCH$_2$CHCHCH$_3$
　　|
　　SCH$_2$COOH

—OCH$_2$CH(SCH$_2$COOH)$_2$

—OCH$_2$CHCH$_2$SCH$_2$CH$_2$OH
　　|
　　SCH$_2$COOH

—OCHCH$_2$SCH$_2$COOH
　　|
　　CH$_2$SCH$_2$COOH

—OCH$_2$CH$_2$CHCH$_2$SCH$_2$COOH
　　　　　　|
　　　　　　SCH$_2$CH$_2$OH

Typical examples of the couplers according to the present invention will be illustrated below.

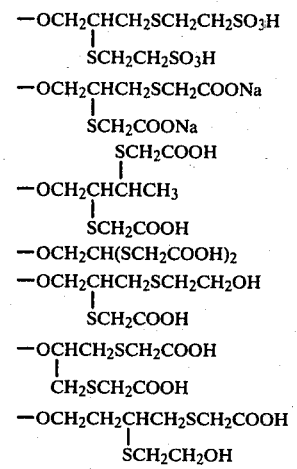

(1)

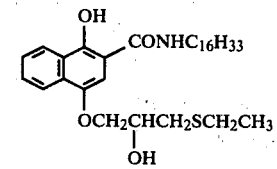

(2)

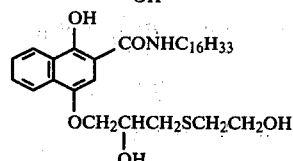

(3)

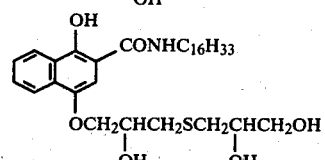

(4)

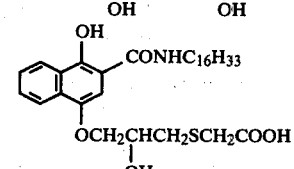

(5)

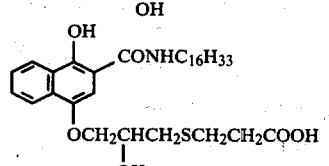

(6)

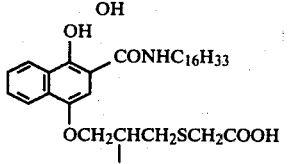

(7)

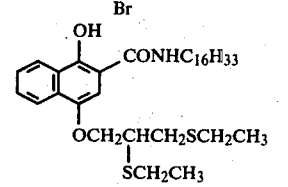

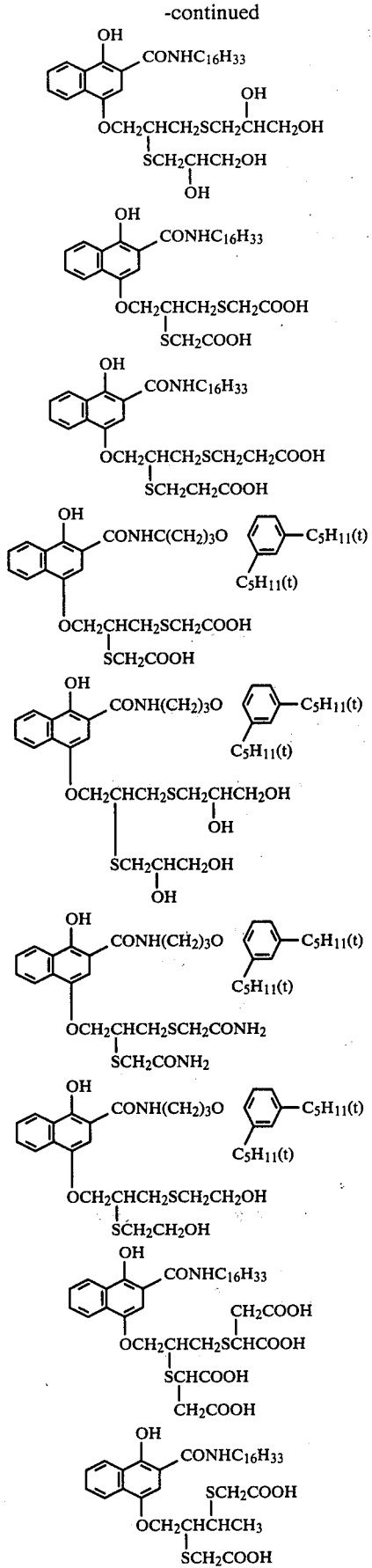
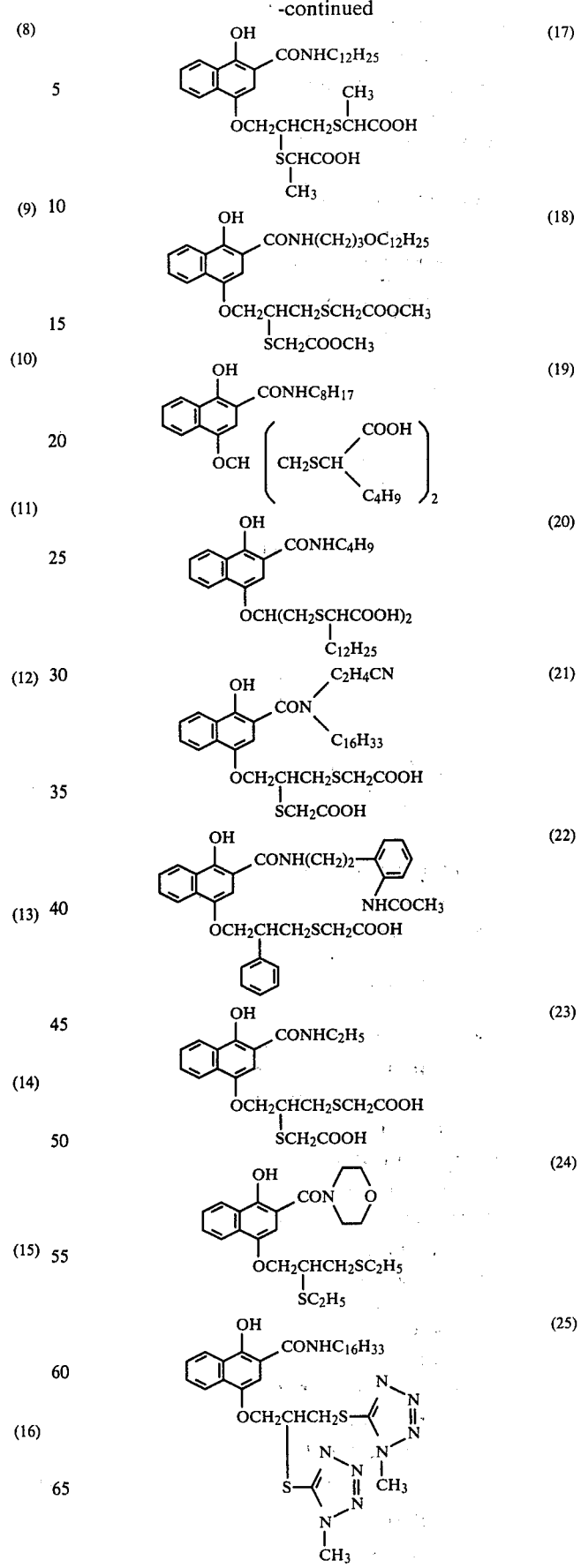

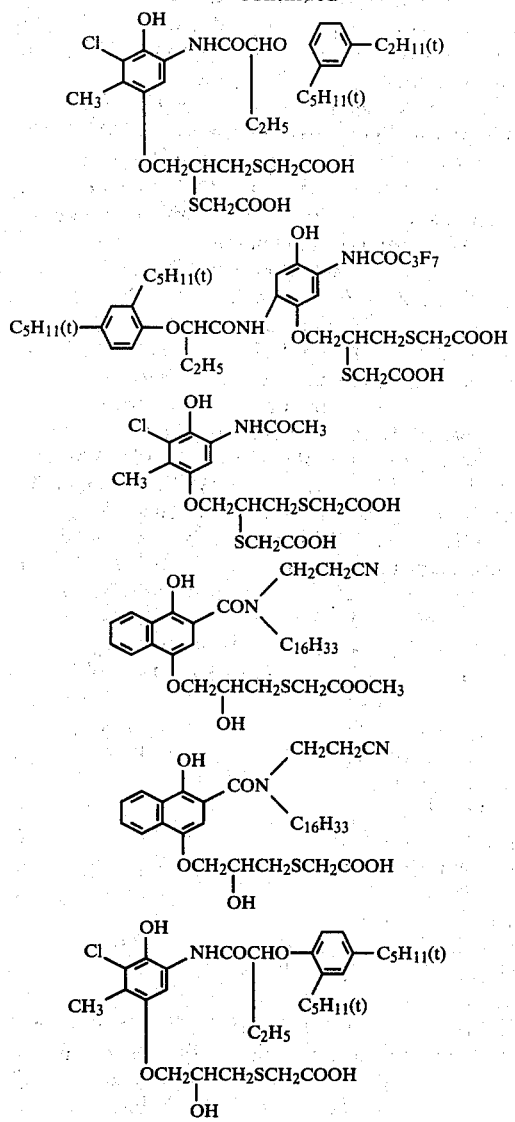

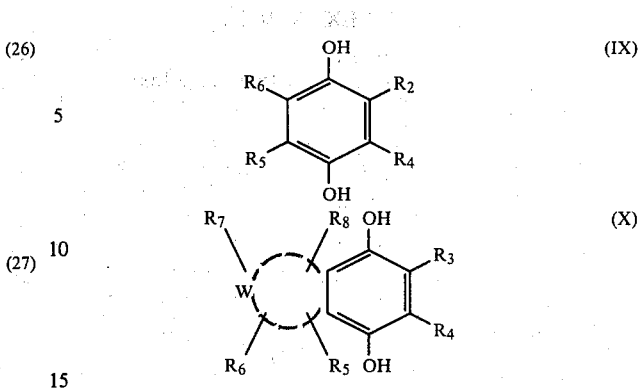

In the above formulae, $R_2$, $R_3$, $R_4$, $R_5$, $R_6$, $R_7$, $R_8$ and W are the same as defined for the formulae (IIA) and (IIB) previously.

Furthermore, cyan couplers can be synthesized by thioetherification of the halo-alkoxy group at the 4-position obtained by the above described haloalkylation.

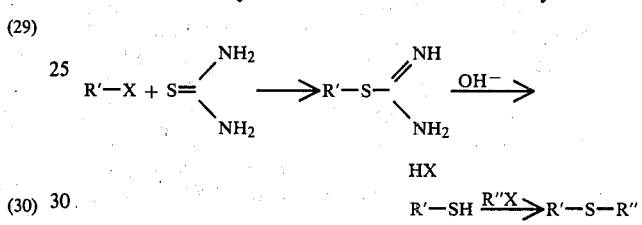

In the above reaction equation formulae, X represents a halogen atom.

With regard to naphtholic couplers, corresponding couplers can be synthesized in the following manner. A 1,4-dihydroxy-2-naphtholic acid is reacted with a halogen-substituted alcohol in toluene in the presence of an acid catalyst. The resulting 1-hydroxy-4-halo-substituted alkoxy-2-naphthoic acid derivative is converted to an acid chloride or a phenyl ester derivative in a conventional manner. The acid chloride or phenyl ester derivative is then condensed with a corresponding amine such as aniline, 2,4-di-tert-amylphenoxypropylamine, etc., to prepare the above described 4-haloalkoxy compound and the latter is subjected to thioetherification in the same manner as described above to form the corresponding coupler.

With regard to phenolic couplers, corresponding couplers can be synthesized as follows. The hydroxy group at the 1-position of a 1,4-dihydroxybenzene derivative is previously protected by, for example, pyranyl etherification or an oxazole ring is previously formed from the hydroxy group at the 1-position and an acetylamino group at the 2-position according to Japanese patent application (OPI) No. 153923/77. The resulting hydroxy-protected compound is reacted with a corresponding alkyl halide in the presence of a basic catalyst to alkylate the hydroxy group at the 4-position. The oxazole ring is then cleaved with an acid and the resulting product is reacted with a corresponding acid chloride in the presence of a dehydrochlorinating agent to form the corresponding coupler.

These compounds according to the present invention can be synthesized according to the following processes.

Both naphtholic and phenolic couplers can be synthesized by reacting a 1,4-dihydroxyaryl derivative represented by the formula (IX) or (X) with a corresponding alkyl halide in a solvent such as acetone, dimethylformamide, methanol, water, etc., in the presence of pyridine, sodium carbonate, sodium hydroxide, a sodium alkoxide, etc., at room temperature or under heating. Alternatively, cyan couplers can be synthesized by reacting a 1,4-dihydroxyaryl derivative with a halogen-substituted alcohol in toluene in the presence of an acid catalyst to haloalkylate the hydroxy group at the 4-position and reacting the latter with a substituted alkylthiol, a substituted arylthiol or a heterocyclic thior in an alcohol in the presence of sodium hydroxide or a sodium alkoxide, etc., at room temperature or under heating.

Typical examples of synthesizing the couplers according to the present invention will specifically be described below.

SYNTHESIS EXAMPLE 1

Synthesis of
1-hydroxy-4-[β,γ-(dicarboxymethylthio)propyloxy]-N-n-hexadecyl-2-naphthamide [Coupler (9)]

60 g (0.3 mol) of 1,4-dihydroxy-2-naphthoic acid was added to 150 ml of 2,3-dibromopropanol and, under heating at 90° C. with stirring, hydrogen chloride gas was bubbled in the mixture during a reaction period of 2 hours. The mixture was cooled to 10° to 20° C. and the crystals precipitated were collected by filteration to obtain 42.4 g (35% yield) of 1-hydroxy-4-(β,γ-dibromopropyloxy)-2-naphthoic acid.

40 g (0.1 mol) of the thus-obtained naphthoic acid derivative, 16.8 g (0.12 mol) of p-nitrophenol and 2.0 ml of dimethylformamide were added to 800 ml of acetonitrile and, under refluxing by heating and stirring, 18.8 g (0.16 mol) of thionyl chloride was added thereto. After reacting for 1 hour, the crystals precipitated were collected by filtration to obtain 50.4 g (0.096 mol) (96% yield) of p-nitrophenyl ester of 1-hydroxy-4-(β,γ-dibromopropyloxy)-2-naphthoic acid.

Then, 31.5 g (0.06 mol) of the thus-obtained p-nitrophenyl ester was reacted with 17.3 g (0.072 mol) of n-hexadecylamine in 300 ml of acetonitrile under heating and stirring. After 2 hours, acetonitrile was distilled off under reduced pressure and methanol was added to the residue. The crystals precipitated were collected by filtration to obtain 31.6 g (84% yield) of 1-hydroxy-4-(β,γ-dibromopropyloxy)-N-n-hexadecyl-2-naphthamide.

Then, 12.5 g (0.02 mol) of the thus-obtained naphthamide compound, 5.5 g (0.06 mol) of the thioglycolic acid and 8.4 g (0.15 mol) of potassium hydroxide were dissolved in a mixture of 100 ml of methanol and 50 ml of water by heating. After refluxing by heating for 3 hours, 100 ml of water was added to the reaction mixture. Under cooling at 10° to 20° C., 10 ml of concentrated hydrochloric acid was added to the mixture and the crystals precipitated were collected by filtration to obtain 11.7 g (90% yield) of the foregoing Coupler (9). Melting Point: 97° to 99° C.

Elemental Analysis for $C_{34}H_{51}NO_7S_2$ Calculated: C: 62.83, H: 7.91, N: 2.16 Found: C: 62.58, H: 7.88, N: 2.14

SYNTHESIS EXAMPLE 2

Synthesis of
1-hydroxy-4-[β-hydroxy-(γ-carboxymethylthio)-propyloxy]-N-n-hexadecyl-2-naphthamide [Coupler (4)]

22 g (0.05 mol) of 1,4-dihydroxy-N-n-hexadecyl-2-naphthamide, 11 g (0.1 mol) of 3-chloro-2-hydroxypropanol and 9 g (0.05 mol) of p-toluenesulfonic acid were added to 200 ml of dehydrated toluene. The mixture was refluxed with heating for 5 hours while removing water formed and then toluene was removed under reduced pressure. By adding 100 ml of methanol to the residue the crystals precipitated were collected by filtration to obtain 20.3 g (0.038 mol) of 4-(γ-chloro-β-hydroxypropyloxy) compound.

Then, 10.4 g (0.02 mol) of the thus-obtained 4-(γ-chloro-β-hydroxypropyloxy) compound, 2.8 g (0.03 mol) of α-thioglycerol and 5.6 g (0.1 mol) of potassium hydroxide were dissolved in a mixture of 100 ml of methanol and 50 ml of water by heating. After refluxing for 3 hours by heating, 100 ml of water was added to the reaction mixture. Under cooling at 10° to 20° C., 10 ml of concentrated hydrochloric acid was added to the mixture and the crystals precipitated were collected by filtration. By recrystallization from a mixture of n-hexane and ethanol, 9.7 g (84% yield) of the foregoing Coupler (4) was obtained. Melting Point: 89° to 90° C.

Elemental Analysis for $C_{32}H_{49}NO_6S$ Calculated: C: 66.75, H: 8.58, N: 2.43 Found: C: 66.48, H: 8.52, N: 2.40

In the production of silver halide color photographic light-sensitive materials using the couplers of the present invention, the couplers may be used alone or in combinations of two or more. Color photographic light-sensitive materials containing the coupler or couplers of the present invention may also contain other additional couplers. For example, such other couplers include cyan dye-forming couplers described in U.S. Pat. Nos. 2,474,293, 3,034,892, 3,592,383, 3,311,476, 3,476,563, etc., compounds capable of releasing a development-inhibiting compound upon color forming reaction (so-called DIR couplers and DIR compounds) (described in, for example, U.S. Pat. Nos. 3,632,345, 3,227,554, 3,379,529, etc.), yellow dye-forming couplers (described in, for example, West German patent application (OLS) No. 2,213,461, U.S. Pat. No. 3,510,306, etc.), and magenta dye-forming couplers (described in, for example, U.S. Pat. No. 3,615,506, Japanese patent application No. 56050/73, and West German patent application (OLS) No. 2,418,959) can be used.

The above-described couplers and the like can be used in combinations of two or more in the same layer to obtain desired characteristics for the light-sensitive materials. It is of course possible to add the same compound to two or more different layers.

Suitable silver halide emulsions which can be used in the present invention include those containing silver chloride and silver bromide as well as mixed halides of silver such as silver chlorobromide, silver iodobromide, silver chloroiodobromide, etc.

The silver halide grains of these emulsions may be of a cubic form, an octahedral form, or may have a mixed crystalline structure.

The silver halide grain size distribution may be narrow or broad, and is not particularly limited. Suitable methods of preparing the silver halide emulsion which can be used include those well known in the art such as the single and double jet process, the controlled double jet process, etc.

Two or more types of silver halide emulsions which have been prepared separately using different processes can be employed. The grain structure of the silver halide may be uniform or different from the surface to the interior, or may be of the so-called "conversion" type as described in British Pat. No. 635,841 and U.S. Pat. No. 3,622,318.

Further, silver halide grains which provide latent images primarily at the surface thereof or in the interior can be employed in the present invention.

The silver halide emulsions used in this invention may be chemically sensitized using well-known chemical sensitizers including sodium thiosulfate, N,N,N'-trimethylthiourea, the complex salts of monovalent gold such as the thiocyanates or the thiosulfates, etc., stannous chloride, hexamethylenetetramine, etc.

The layers of the photographic material can be coated using any known coating method including dip coating, air-knife coating, curtain coating, extrusion coating using a hopper as described in U.S. Pat. No. 2,681,294 and using a simultaneous multi-layer coating as set forth in U.S. Pat. Nos. 3,761,791, 3,508,947, 2,941,898, 3,526,528, etc.

Suitable hydrophilic high molecular weight materials which can be present in the photographic coatings of the present invention include gelatin, cellulose derivatives, such as carboxymethylcellulose, hydroxyethylcellulose, etc., carbohydrate derivatives, such as starch derivatives, synthetic hydrophilic colloid materials, such as poly(vinyl alcohol), poly(N-vinylpyrrolidone), copolymers containing acrylic acid, polyacrylamide and the derivatives or partially hydrolyzed products of the above-described polymers, etc. Of these, the most representative is gelatin and gelatin is most generally used. The gelatin can be partly or completely replaced by a synthetic polymer or a gelatin derivative.

The color photographic materials of the present invention may comprise photographic emulsions spectrally sensitized or supersensitized so as to be sensitive to blue, green or red light using cyanine dyes, such as cyanine, merocyanine, carbocyanine, etc., dyes, alone or as combinations thereof or in combination with styryl dyes. Descriptions of suitable spectral sensitization techniques appear in, for example, U.S. Pat. No. 2,493,748 for the blue region, U.S. Pat. No. 2,688,545 for the green region and U.S. Pat. No. 3,511,664 for the red region.

The photographic emulsion containing the coupler of the present invention can contain known stabilizers or anti-fogging agents (e.g., 4-hydroxy-6-methyl-1,3,3a,7-tetrazaindene, 3-methylbenzothiazole, 1-phenyl-5-mercaptotetrazole, mercury-containing compounds, mercapto compounds, metallic salts, etc.).

A synthetic polymeric material can be mixed with the hydrophilic colloid such as gelatin in the photographic emulsion layer and other layers of the photographic color material of the present invention. A typical example of such as polymeric material is an aqueous latex of vinyl polymers as disclosed in U.S. Pat. No. 2,376,005, etc.

Formation of dye images in accordance with the present invention can be realized in various forms of light-sensitive materials. One of them is a process of forming a water-insoluble or diffusion-resistant dye image in an emulsion layer by processing a silver halide light-sensitive material with a color developer containing dissolved therein an aromatic primary amine color-developing agent and a coupler, which process is a coupler-in-developer type color photographic process. For example, illustrative couplers (23) and (28) can be used for such process. Another one is a process of forming a water-insoluble or diffusion resistant dye image in an emulsion layer by processing a light-sensitive material comprising a support having provided thereon a silver halide emulsion layer containing a diffusion-resistant coupler, with an alkaline developer containing an aromatic primary amine color-developing agent. For example, illustrative couplers (4), (9), (17), (21), etc., can be used for this process.

The phenolic or α-naphtholic couplers used in the present invention are dissolved in an aqueous medium or an organic solvent, and then dispersed in the photographic emulsion.

Of the couplers of the invention, oil-soluble, diffusion-resistant couplers used for an incorporated-in type process are first dissolved in an organic solvent, then dispersed as fine colloidal particles in a photographic emulsion for incorporation into a light-sensitive material.

It is most preferred to dissolve oil-soluble, diffusion-resistant couplers in an organic solvent, and add the resulting solution to a photographic emulsion, to provide the best effect according to this invention.

Oil-soluble diffusion-resistant couplers represented by the formulae (IIA) and (IIB) are those wherein one of the substituents represented by $R_1$ through $R_8$ represents a group having a ballast group containing a $C_8$ to $C_{30}$ hydrophobic residue which is bonded to the coupler skeletal structure directly or via an imino bond, an ether bond, a thioether bond, a carbonamido bond, a sulfonamido bond, a uredio bond, an ester bond, a carbonyl bond, an imido bond, a carbamoyl bond, a sulfamoyl bond, or the like.

Examples of such a ballast group include an alkyl group, an alkoxyalkyl group, an alkenyl group, an alkyl-substituted aryl group, an alkoxy-substituted aryl group, a terphenyl group, etc. These ballast groups may be substituted by a halogen atom (e.g., a fluorine atom, a chlorine atom, etc.), a nitro group, an amino group, a cyano group, an alkoxycarbonyl group, an aryloxycarbonyl group, an amido group, a carbamoyl group, a sulfamoyl group, a ureido group, a sulfonamido group, or the like. Specific examples of the ballast group include a 2-ethylhexyl group, a tert-octyl group, an n-dodecyl group, a 2,2-dimethyldodecyl group, an n-octadecyl group, a 2-(n-hexyl)decyl group, a 9,10-dichlorooctadecyl group, a 2,4-di-tert-amylcyclohexyl group, a dodecyloxypropyl group, an oleyl group, a 2,4-di-tert-amylphenyl group, a 2,4-di-tert-amyl-6-chlorophenyl group, a 3-pentadecylphenyl group, a 2-dodecyloxyphenyl group, a 3-heptadecyloxyphenyl group, a perfluoroheptyl group, and so forth.

A specific and suitable manner for dispersing the above-described diffusion-resistant couplers in a photographic emulsion is described in detail in U.S. Pat. No. 3,676,131. An organic solvent having low solubility in water, a high boiling point, and compatible with the couplers in a color light-sensitive material such as substituted hydrocarbons, carboxylic acid esters, carboxylic acid amides, phosphoric acid esters, and ethers may be used to dissolve the couplers. Specific examples thereof include di-n-butyl phthalate, diisooctyl acetate, di-n-butyl sebacate, tricresyl phosphate, tri-n-hexyl phosphate, tricyclohexyl phosphate, N,N-diethylcaprylamide, butyl-n-pentadecylphenyl ether, chlorinated paraffin, butyl benzoate, pentyl o-methylbenzoate, propyl 2,4-dichlorobenzoate, etc. It is advantageous to use, in addition to the above-described high boiling solvents, an auxiliary solvent which helps dissolve the couplers and which can be removed during the production of light-sensitive materials. Examples of such auxiliary solvent include propylene carbonate, ethyl acetate, butyl acetate, cyclohexanol, tetrahydrofuran, cyclohexanone, etc.

The use of a surface active agent is advantageous to assist in finely dispersing these oil-soluble couplers in a hydrophilic high molecular material to be used in a photographic emulsion. In particular, anionic surface active agents such as sodium cetylsulfate, sodium p-dodecylbenzenesulfonate, sodium nonylnaphthalenesulfonate, sodium di(2-ethylhexyl)-α-sulfosuccinate, etc., and nonionic surface active agents such as sorbitan sesquioleic acid ester, sorbitan monolauric acid ester, etc., are suitable.

A homogenizer for an emulsion, a colloid mill, an ultrasonic wave emulsifier, and the like are useful for dispersing the oil-soluble couplers.

Examples of silver halide light-sensitive materials in which the coupler of the present invention can be used include color negative films, color positive films, color reversal films, color reversal papers, color papers and other color photographic products for general use. Further, the couplers of the present invention can be used in color direct positive products, monochromatic products, color radiographic products, and so forth.

The couplers of the present invention can be used in multilayer color photographic materials of the conventional type (e.g., those described in U.S. Pat. Nos. 3,726,681, 3,516,831, British Pat. No. 818,687 and 923,045, etc.), in the process set forth in Japanese Patent Application (OPI) No. 5179/75, and also in the methods disclosed in German Patent Application (OLS) No. 2,322,165 and U.S. Pat. No. 3,703,375 in which they are used in combination with a DIR compound.

The amount of the coupler used is generally in the range of from about 1 to 1,500 g per mol of silver halide, which, however, can be changed according to the specific end-uses.

Silver halide photographic materials of the present invention comprise a support and various coatings thereon, such as a silver halide emulsion layer, an intermediate layer, an antihalation layer, a protective layer, a yellow filter layer, a backing layer, a mordanting polymer layer, a layer for preventing stains by the developer, etc. The silver halide emulsion layers for color photography comprise a red sensitive silver halide emulsion layer, a green sensitive silver halide emulsion layer and a blue sensitive silver halide emulsion layer. There is no particular limitation on the layer arrangement thereof, and furthermore each of these layers can be divided into two or more layers.

From the point of view of obtaining increased stability of color photographic pictures, it is advantageous for the light-sensitive material of the present invention to contain a p-substituted phenol derivative in an emulsion layer or a neighboring layer. Particularly preferred p-substituted phenol derivatives can be selected from among hydroquinone derivatives described in U.S. Pat. Nos. 2,360,290, 2,418,613, 2,675,314, 2,701,197, 2,704,713, 2,710,801, 2,728,659, 2,732,300, 2,735,765, 2,816,028, etc.; gallic acid derivatives as described in U.S. Pat. Nos. 3,457,097, 3,069,262, and Japanese Patent Publication No. 13496/68; p-alkoxyphenols as described in U.S. Pat. No. 2,735,765 and Japanese Patent Application (OPI) No. 4738/72; and p-hydroxyphenol derivatives as described in U.S. Pat. Nos. 3,432,300, 3,573,050, 3,574,627 and 3,764,337.

The light-sensitive material used in the invention advantageously contains an ultraviolet ray absorbent described in, for example, U.S. Pat. Nos. 3,250,617, 3,253,921, etc., in an emulsion layer or a neighboring layer for stabilizing images.

The silver halide emulsion and other layers can be hardened using any conventionally known methods employing, e.g., aldehyde compounds such as formaldehyde, glutaraldehyde, etc., ketone compounds, such as diacetyl or cyclopentanedione, compounds having a reactive halogen, such as bis(2-chloroethylurea), 2-hydroxy-4,6-dichloro-1,3,5-triazine, and those described in U.S. Pat. Nos. 3,288,775, 2,732,303, 3,125,449 and 1,167,207, compounds having a reactive olefinic group, such as divinyl sulfone, 5-acetyl-1,3-diacryloyl-hexahydro-1,3,5-triazine, and those set forth in U.S. Pat. Nos. 3,635,718 and 3,232,763, British Pat. No. 994,869, etc., N-methylol compounds, such as N-hydroxymethyl phthalimide and those set forth in U.S. Pat. Nos. 2,732,316 and 2,586,168, etc., isocyanate compounds disclosed in U.S. Pat. No. 3,103,437, aziridine compounds set forth in U.S. Pat. Nos. 3,017,280 and 2,983,611, etc., acid derivatives carbobiimide derivatives such as those described in U.S. Pat. No. 3,100,702, etc., epoxy compounds set forth in, for example, U.S. Pat. No. 3,091,537, isoxazoles disclosed in U.S. Pat. Nos. 3,321,313 and 3,543,292, halocarboxyaldehyde compounds including nucochloric acid, dioxane derivatives such as dihydroxydioxane, dichlorodioxane, etc., or inorganic hardening agents such as chrome alum, zirconium sulfate, etc.

Precursors of hardening agents can also be used with examples of such precursors including alkali metal bisulfite/aldehyde adducts, the methylol derivative of hydantoin, primary aliphatic nitro alcohols, etc.

The color photographic light-sensitive material of the present invention can be subjected to conventional and well known processings comprising, after exposure, color development, bleaching and fixing. Processing step may be combined with other processing step using a processing agent capable of accomplishing the corresponding functions of the separate steps. A typical example of such a combined processing is a mono-bath process using a blix solution.

Depending on the requirements, the development processing can include additional steps such as pre-hardening, neutralization, primary development (black-and-white development), image stabilization, washing with water, etc. The processing temperature, which is determined depending on the kind of photographic material as well as by the processing composition, is variable but, in most cases, is not lower than 18° C.

A particularly useful temperature range is from about 20° to 60° C. The temperature may be varied from one processing step to another in the processing.

A color developer comprises an aqueous alkaline solution with a pH not lower than about 8, and more preferably between 9 and 12, containing a color developing agent the oxidation product of which is capable of reacting with a coupler to form a dye.

Suitable color developing agents which can be used include, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfamidoethylaniline, 4-amino-N,N-dimethylaniline, 4-amino-3-methoxy-N,N-diethylaniline, 4-amino-3-methyl-N-ethyl-N-$\beta$-methoxyethylaniline, 4-amino-3-methoxy-N-ethyl-N-$\beta$-methoxyethylaniline, 4-amino-3-$\beta$-methanesulfamidoethyl-N,N-diethylaniline, and the salts thereof, such as the sulfates, the hydrochlorides, the sulfites, the p-toluenesulfonates, etc. Other color developing agents which can be used are described in U.S. Pat. Nos. 2,592,364 and 2,193,015, Japanese patent application (OPI) No. 64933/73, L. F. A. Mason, Photographic Processing Chemistry, pp. 226–229, Focal Press, London (1966), etc.

Each of the above-described compounds can be used in conjunction with 3-pyrazolidone derivatives. Further, a number of additives well known in the art may be present in the color developer.

The photographic material of the present invention is subjected to bleaching after color development. This step may be combined with fixing, whereby the processing solution contains a fixing agent in addition to a bleaching agent.

Suitable bleaching agents include ferricyanide salts, bichromate salts, water-soluble cobalt (III) salts, water-soluble copper (II) salts, water-soluble quinones, nitrosophenol, polyvalent metal compounds containing Fe (III), Co (III), Cu (II), with complex salts of such metals with organic acids, such as, for example, ethylenediamine tetraacetic acid, nitrilotriacetic acid, imidoacetic acid, N-hydroxyethylenediamine triacetic acid and other aminopolycarboxylic acid, malonic acid, tartaric acid, malic acid, diglycolic acid, dithioglycolic acid and 2,6-dipicolic acid copper complex salt, etc., being particularly preferred, peracids, such as alkyl peracids, persulfates, permanganates, hydrogen peroxide, etc., hypochlorites, etc.

Other additives, such as bleach accelerating agents as disclosed in U.S. Pat. Nos. 3,042,520 and 3,241,966, Japanese Patent Publication Nos. 8506/70 and 8836/70, etc., can be further added to the bleaching solution.

It has been found that the couplers in accordance with the invention can be used even for silver halide photographic materials of the low silver content type in which the amount of silver halide in the emulsion is from several tenths to one hundred times smaller than that of the ordinary photographic material. Using such a photosensitive material, color images of sufficiently high density can be obtained using the color intensification process in which a peroxide or a cobalt complex salt is employed (for example, as disclosed in German Patent application (OLS) No. 2,357,694, U.S. Pat. No. 3,674,490 and 3,761,265, German patent application (OLS) Nos. 2,044,833, 2,056,359, 2,056,360 and 2,226,770, Japanese patent application (OPI) Nos. 9728/73 and 9729/73, etc.).

The invention will now be described in more detail by reference to examples which, however, do not limit the present invention in any way.

EXAMPLE 1

10 g of the foregoing Coupler (1), i.e., 1-hydroxy-4-($\beta$-hydroxy-$\gamma$-ethylthiopropyloxy)-N-n-hexadecyl-2-naphthamide was added to a mixture of 10 ml of di-n-butyl phthalate and 20 ml of ethyl acetate and dissolved by heating to 50° C. The resulting solution was added to 100 ml of an aqueous solution containing 10 g of gelatin and 0.5 g of sodium p-dodecylbenzenesulfonate, and subjected to vigorous mechanical stirring for 20 minutes using a high speed agitator to thereby finely emulsify and disperse the coupler together with the solvent. (The resulting emulsion is referred to as emulsion dispersion (I)).

61.4 g of this fine emulsion dispersion (I) was added to 100 g of a photographic emulsion containing 0.03 mol of silver chlorobromide (AgBr: 50 mol%) and 8 g of gelatin, and 12 ml of a 2% aqueous solution of 2-hydroxy-4,6-dichloro-s-triazine sodium salt was added thereto as a hardener. Then, the pH was adjusted to 6.5, and the resulting emulsion was coated on a cellulose triacetate film base in a coated silver amount of $8.5 \times 10^{-3}$ mol/m² to prepare a photographic light-sensitive material, which was called sample I. The coupler content in sample I was $2.16 \times 10^{-3}$ mol/m².

Then, in a manner analogous to the above-described process for emulsion dispersion (I) except using 10 g of the foregoing Couplers (2) and (4), there were prepared emulsion dispersions (II) and (III), respectively. Photographic light-sensitive materials were prepared in the same manner as with sample I using the same photographic emulsion except for adding 63.0 g of emulsion dispersion (II) and 64.7 g of emulsion dispersion (III), respectively. The resulting two samples were referred to as samples II and III, respectively.

As comparative samples, photographic light-sensitive materials were prepared in the same manner as with sample I except for using 10 g of 1-hydroxy-4-propyloxy-N-n-hexadecyl-2-naphthamide (coupler a) and 10 g of 1-hydroxy-4-butoxy-N-n-hexadecyl-2-naphthamide (coupler b), respectively, and adding 52.9 g and 54.1 g of the emulsion dispersion, respectively. The resulting samples were referred to as samples A and B.

Coupler contents in these samples II, III, A and B were $2.14 \times 10^{-3}$ mol/m², $2.14 \times 10^{-3}$ mol/m², $2.16 \times 10^{-3}$ mol/m², and $2.12 \times 10^{-3}$ mol/m², respectively.

These photographic light-sensitive materials were subjected to stepwise exposure for sensitometry, then to the following processing steps in the order described.

| | Temperature (°C.) | Time (minutes) |
|---|---|---|
| 1. Color development | 24 | 8 |
| 2. Washing with water | " | 1 |
| 3. First fixing | " | 4 |
| 4. Washing with water | " | 3 |
| 5. Bleaching | " | 3 |
| 6. Washing with water | " | 3 |
| 7. Second fixing | " | 4 |
| 8. Washing with water | " | 10 |

The composition of the color developer used in the above-described color development processing was as follows.

| Color Developer | |
|---|---|
| Anhydrous Sodium Sulfite | 3.0 g |
| 4-Amino-3-methyl-N,N-diethylaniline Hydrochloride | 2.5 g |
| Sodium Carbonate (monohydrate) | 47.0 g |
| Potassium Bromide | 2.0 g |
| Water to make | 1,000 ml |

The fixing solution and the bleaching solution had the following compositions, respectively.

| Fixing Solution (first and second fixing solutions) | |
|---|---|
| Sodium Thiosulfate | 150 g |
| Sodium Sulfite | 15 g |
| Glacial Acetic Acid (28% aq. soln.) | 48 ml |
| Boric Acid | 7.5 g |
| Water to make | 1,000 ml |
| Bleaching Solution | |
| Potassium Bromide | 20 g |
| Potassium Ferrycyanide | 100 g |
| Glacial Acetic Acid | 20 ml |
| Sodium Acetate | 40 g |
| Water to make | 1,000 ml |

After the above described processing steps, the optical densities of these samples I, II, III, A and B with respect to red light (wavelength ≃640 nm) were measured to obtain the results tabulated in Table 1.

TABLE 1

| Film Sample | Coupler | Amount of Coupler (mol/m²) | Fog | Sensitivity (Relative value) | Gamma | Maximum Density |
|---|---|---|---|---|---|---|
| I | (1) | $2.16 \times 10^{-3}$ | 0.05 | 100 | 3.27 | 3.49 |

TABLE 1-continued

| Film Sample | Coupler | Amount of Coupler (mol/m$^2$) | Fog | Sensitivity (Relative value) | Gamma | Maximum Density |
|---|---|---|---|---|---|---|
| II | (2) | 2.14 × 10$^{-3}$ | 0.05 | 125 | 3.42 | 3.57 |
| III | (4) | 2.14 × 10$^{-3}$ | 0.06 | 140 | 3.96 | 3.85 |
| A | (a) | 2.16 × 10$^{-3}$ | 0.05 | 75 | 1.80 | 2.41 |
| B | (b) | 2.12 × 10$^{-3}$ | 0.04 | 68 | 1.68 | 2.23 |

*Relative values of reciprocals of exposure amounts necessary to obtain a density of fog + 0.1.

Separately, samples I, II, III, A and B were processed changing the time of the color development, and maximum densities for red light were measured to obtain the results shown in Table 2.

TABLE 2

| Film Sample | Coupler | Developing Time (minutes) 4 | 8 | 15 |
|---|---|---|---|---|
| I | (1)* | 3.37 | 3.49 | 3.51 |
| II | (2)* | 3.49 | 3.57 | 3.59 |
| III | (4)* | 3.82 | 3.85 | 3.85 |
| A | (a)** | 2.12 | 2.41 | 2.62 |
| B | (b)** | 1.94 | 2.23 | 2.40 |

*Present Invention
**Comparative coupler

These results show that as compared with coupler (a) wherein an coupling site is substituted by a propyloxy group and coupler (b) wherein an active site is substituted by a butoxy group used in the comparative samples the couplers of this invention provide a high sensitivity, high gradation of density, and high color density, and they provide sufficient color formation in a short time so that the processing time can be shortened. In order to more clearly show the improved coupling reactivity, the following experiments were conducted.

Samples obtained in the same manner as with sample I using, respectively, mixtures prepared by mixing the foregoing Couplers (1), (2), (4) of the present invention, coupler (a) and coupler (b) with a yellow color-forming coupler (c), α-(4-methoxybenzoyl)-2-chloro-5-[α-(2',4'-di-tert-amylphenoxy)butyramido]acetanilide, in a molar ratio of 1:2 were subjected to the action of a color developing agent of 4-amino-3-methyl-N,N-diethylaniline to competitively form color. The relative reaction rate constants of the coupling reaction of the couplers of the present invention based on yellow color-forming coupler (c) were calculated by analyzing the ratio of the amount of the yellow dye to that of the cyan dye formed.

Coupling reactivity of the coupler can be determined as a relative value by adding in combination two couplers M and N providing dyes distinctly discriminatable from each other to an emulsion, and measuring each of the amounts of dyes obtained by color-developing the emulsion.

Suppose that coupler M provides a maximum density of $(DM)_{max}$ and a medium density of DM, and that coupler N provides $(DN)_{max}$ and DN, respectively. Then, the reactivity ratio of the two couplers, RM/RN, can be represented by the following formula:

$$\frac{RM}{RN} = \frac{\log\left(1 - \frac{DM}{(DM)_{max}}\right)}{\log\left(1 - \frac{DN}{(DN)_{max}}\right)}$$

That is, the coupling reactivity ratio, RM/RN, can be determined from the slope of a straight line obtained by plotting several sets of DM and DN, obtained by stepwise exposing the emulsion containing mixed couplers and development processing on two rectangular coordinate axes as $$\log\left(1 - \frac{D}{D_{max}}\right)$$

As a result, it was found that relative reaction rate constants of couplers of the present invention (1), (2) and (4) were 2.3, 2.9 and 3.5, respectively, whereas that of conventionally known coupler (a) substituted by a propyloxy group in an active site was 0.9 and that of butoxy substituted coupler (b) was 0.8. Thus, it is clearly demonstrated that the couplers of the present invention have an improved reactivity and are excellent couplers.

EXAMPLE 2

10 g of the foregoing coupler (11), i.e., 1-hydroxy-4-[β,γ-(dicarboxymethylthio)propyloxy]-N-[γ-(2,4-di-tertamylphenoxy)propyl]-2-naphthamide was added to a mixture of 10 ml of tricresyl phosphate, 20 ml of ethyl acetate, and 0.5 g of sodium di(2-ethylhexyl)-α-sulfosuccinate and, after heating to 50° C. to dissolve, the mixture was added to 100 ml of an aqueous solution containing 10 g of gelatin, then finely emulsified and dispersed using a homogenizer to obtain an emulsion dispersion which was referred to as emulsion dispersion (IV).

49.6 g of this fine emulsion dispersion was added to 100 g of a silver bromoiodide emulsion (gelatin content: 6 g) containing 7 mol% iodide and 3.5 × 10$^{-2}$ mol silver. Then, to the resulting mixture was added 5 ml of a 2% methanol solution of 6-methyl-4-hydroxy-1,3,3a,7-tetraazaindene and 6.5 ml of a 2% aqueous solution of 2-hydroxy-4,6-dichloro-s-triazine sodium salt (as a hardener) and, finally, the pH was adjusted to 6.5. The resulting mixture was coated on a cellulose triacetate base in a coated coupler amount of 2.05 × 10$^{-3}$ mol/m$^2$ to obtain sample IV.

Then, the foregoing couplers (14), (12) and (9) and comparative couplers (d), (e), (f), (g) and (h) (as comparative couplers identified below) were used and, in the same manner as with emulsion dispersion (IV), emulsion dispersions (V), (VI), (VII), (D), (E), (F), (G) and (H) corresponding to couplers (14), (12), (9), (d), (e), (f), (g) and (h), respectively were prepared. Then, there were prepared samples V, VI, VII, D, E, F, G and H containing 45.1 g of emulsion dispersion (V) and 100 g of the same emulsion as used in sample IV, 49.4 g of emulsion dispersion (VI) and 100 g of the same emulsion, 46.3 g of emulsion dispersion (VII) and 100 g of the same emulsion, 32.4 g of emulsion dispersion (D) and 200 g of the emulsion, 41.3 g of emulsion dispersion (E) and 100 g of the emulsion, 50.0 g of emulsion dispersion (F) and 100 g of the emulsion, 41.9 g of emulsion dispersion (G) and 100 g of the emulsion, and 41.8 g of emulsion dispersion (H) and 100 g of the emulsion, respectively.

The coupler contents in these eight samples were shown in Table 3 below.

These nine samples were stepwise exposed, and then subjected to the following processing steps.

| Processing Step | Temperature (°C.) | Time |
|---|---|---|
| 1. Color development | 38 | 3 min. 15 sec. |
| 2. Bleaching | " | 6 min. 30 sec. |
| 3. Washing with water | " | 2 min. |
| 4. Fixing | " | 4 min. |
| 5. Washing | " | 4 min. |
| 6. Stabilizing bath | " | 1 min. |

The processing solutions used had the following compositions.

| Color Developer Solution | |
|---|---|
| 4-Amino-N-ethyl-N-(-β- methanesulfonamidoethyl)aniline Monosulfate | 5 g |
| Sodium Sulfite | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |
| To adjust pH to 10.1 | |
| Water to make | 1,000 ml |
| Bleaching Solution | |
| Iron (III) Ammonium Ethylenediamine- tetraacetate | 100 g |
| Disodium Ethylenediamine tetraacetate | 10 g |
| Potassium Bromide | 150 g |
| Glacial Acetic Acid | 10 g |
| Aqueous Ammonia to adjust pH to 6.0 | |
| Water to make | 1 l |
| Fixing Solution | |
| Ammonium Thiosulfate | 150 g |
| Sodium Sulfite | 10 g |
| Sodium Hydrogen Sulfite | 2.5 g |
| To adjust pH to 6.0 | |
| Water to make | 1 l |
| Stablilizing Bath | |
| Formalin (37%) | 5 ml |
| Fuji Drywell | 3 ml |
| Water to make | 1 l |

After the above-described processing, optical densities of these samples IV, V, VI, VII, D, E, F, G and H for red light were measured to obtain the results shown in Table 3.

From the results shown in Table 3, it is apparent that cyan couplers having an coupling-off group represented by the formula (I) according to the invention have superior properties with respect to sensitivity, gamma and maximum density in comparison with the known couplers.

TABLE 3

| Film Sample | Coupler | Amount of Coupler (mol/m$^2$) | Fog | Sensitivity* (Relative values) | Gamma | Maximum Density |
|---|---|---|---|---|---|---|
| IV | (11)** | 2.05 × 10$^{-3}$ | 0.06 | 98 | 2.82 | 3.38 |
| V | (14)** | 2.07 × 10$^{-3}$ | 0.06 | 91 | 2.70 | 3.31 |
| VI | (12)** | 2.04 × 10$^{-3}$ | 0.06 | 95 | 2.75 | 3.35 |
| VII | (9)** | 2.08 × 10$^{-3}$ | 0.06 | 100 | 2.83 | 3.40 |
| D | (d)*** | 2.05 × 10$^{-3}$ | 0.06 | 62 | 1.55 | 2.35 |

TABLE 3-continued

| Film Sample | Coupler | Amount of Coupler (mol/m$^2$) | Fog | Sensitivity* (Relative values) | Gamma | Maximum Density |
|---|---|---|---|---|---|---|
| E | (e)*** | 2.05 × 10$^{-3}$ | 0.06 | 65 | 1.81 | 2.45 |
| F | (f)*** | 2.06 × 10$^{-3}$ | 0.07 | 71 | 1.93 | 2.42 |
| G | (g)*** | 2.07 × 10$^{-3}$ | 0.06 | 68 | 1.85 | 2.31 |
| H | (h)*** | 2.04 × 10$^{-3}$ | 0.06 | 80 | 2.12 | 2.65 |

*Relative values of reciprocals of exposure amounts necessary for obtaining a density of fog + 0.1.
**Present invention
***Comparative coupler The comparative couplers used were as follows:

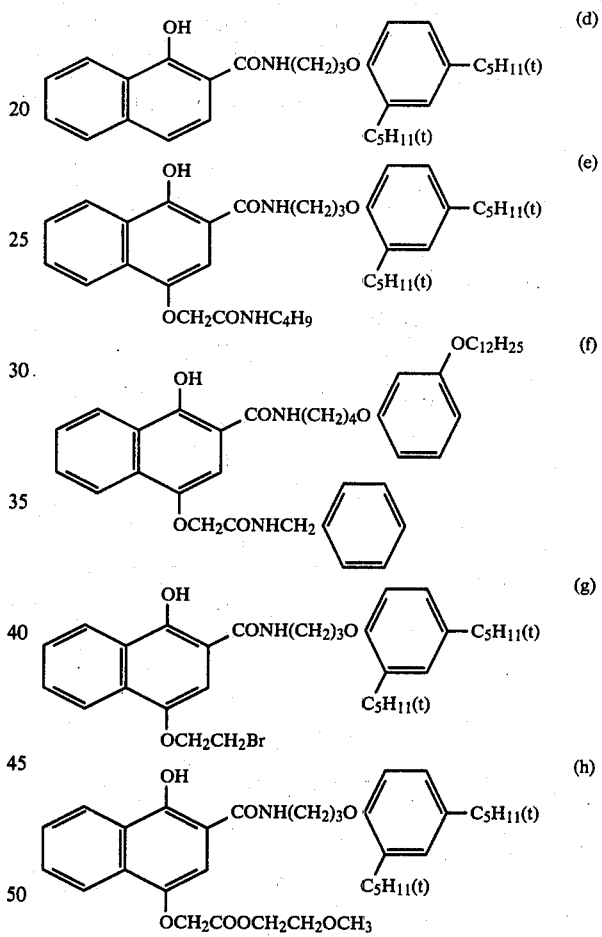

EXAMPLE 3

Emulsion dispersions (J), (K), (L) and (M) were prepared using the comparative couplers (j), (k), (l) and (m) described below, respectively. Each of the emulsion dispersions and the emulsion dispersions (IV), (V), (VI), (VII) and (VIII) was stirred at 40° C., coated on a subbed glass plate and dried with cool air. The transparency of the plates was observed and the results are shown in Table 4.

TABLE 4

| Coupler | Transparency | | | |
|---|---|---|---|---|
| | 1 hour | 3 hour | 10 hour | 24 hour |
| (11)* | o | o | o | o |
| (14)* | o | o | o | o |

TABLE 4-continued

| Coupler | Transparency | | | |
|---|---|---|---|---|
| | 1 hour | 3 hour | 10 hour | 24 hour |
| (12)* | o | o | o | o |
| (9)* | o | o | o | o |
| (j)** | o | x | — | — |
| (k)** | o | o | x | — |
| (l)** | o | o | x | — |
| (m)** | o | x | — | — |

*Present Invention
**Comparative Coupler
o: Turbidity was not observed (Emulsion dispersion was stable)
x: Turbidity was observed (Emulsion dispersion was not stable, or deposition of the couplers was observed)

From the above results, it is apparent that the couplers according to the present invention have a high dispersion stability in comparison with the comparative couplers, or, in other words, they have extremely good dispersion properties.

The comparative couplers used were as follows:

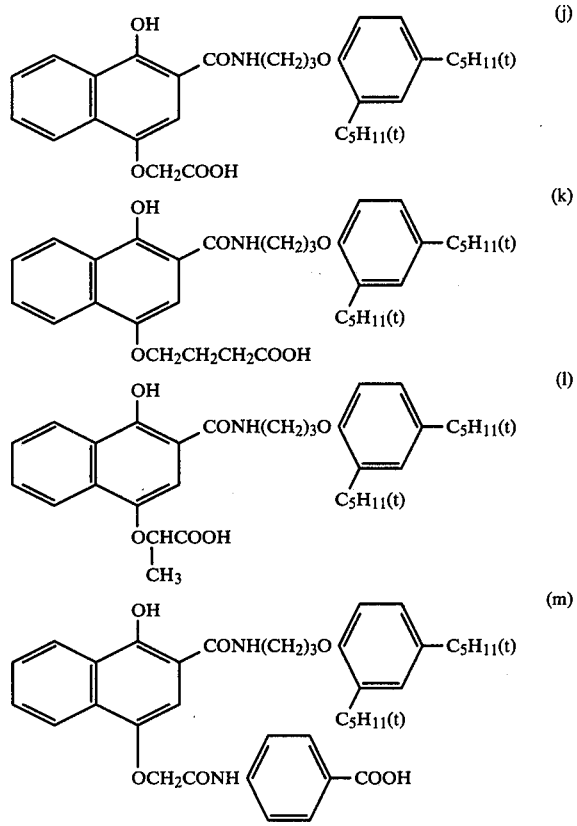

EXAMPLE 4

50.2 g of the foregoing coupler (26), i.e., 2-chloro-3-methyl-4-[β,γ-(dicarboxymethylthio)propyloxy]-6-[α-(2,4-di-tert-amylphenoxy)butylramido]phenol, 40 ml of di-n-butyl phthalate, 80 ml of ethyl acetate, and 2.0 g of sodium di(2-ethylhexyl)-α-sulfosuccinate were mixed and heated to 50° C. to dissolve. The resulting solution was added to 400 ml of an aqueous solution containing 40 g of gelatin, and the thus-obtained emulsion was further finely emulsified and dispersed using a homogenizer.

An emulsion to be used was prepared by adding as a red sensitive sensitizing dye 200 ml of a 0.01% methanol solution of compound I-6 as described in Japanese Patent Publication No. 22189/70 to 1.0 kg of a silver chlorobromide emulsion containing 50 mol% bromide, 0.3 ml silver, and 70 g gelatin, then adding thereto 50 ml of a 1% methanol solution of 6-methyl-4-hydroxy-1,3,3a,7-tetrazaindene.

To this emulsion was added the whole amount of the above-described emulsion dispersion, and 30 ml of a 3% acetone solution of triethylenephosphamide was added thereto as a hardener. Finally, the pH was adjusted to 6.5 to prepare a red sensitive silver halide emulsion.

On a support of baryta paper resin-treated on both sides with polyethylene were coated, as a first layer, a blue-sensitive silver halide emulsion containing coupler (n), i.e., α-(5,5-dimethyl-2,4-dioxooxazolidin-3-yl)-α-pivaloyl-2-chloro-5-[α-(2',4'-di-tert-amylphenoxy)-butyramido]acetanilide in a dry thickness of 4.0μ and, as a second layer, a gelatin solution in a dry thickness of 1.0μ and, as a third layer, a green-sensitive silver halide emulsion containing coupler (p), i.e., 1-(2,4,6-trichlorophenyl)-3-[(2-chloro-5-n-tetradecanamido)-anilino]-5-pyrazolone in a dry thickness of 2.5μ. As a fourth layer, a gelatin solution containing 2-(2'-benzotriazolyl)-4,6-dibutylphenol as an ultraviolet ray absorbent was coated thereon in a dry thickness of 2.5μ. As a fifth layer, the aforesaid red-sensitive silver halide emulsion was coated in a dry thickness of 3.5μ. Further, as an uppermost layer, a gelatin solution was coated thereon in a dry thickness of 0.5μ to prepare a color photographic paper.

A color negative image was optically printed on this color photographic paper followed by subjecting the paper to the following processing steps.

| Processing Step | Temperature (°C.) | Time |
|---|---|---|
| 1. Color development | 33 | 3 min. 30 sec. |
| 2. Bleach-fixing | 33 | 1 min. 30 sec. |
| 3. Washing with water | 25 to 30 | 2 min. 30 sec. |

Each of the processing solution used had the following composition.

| Color Developer Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N-ethyl-N-(β-methanesulfonamido-ethyl)-m-toluidine Sesquisulfate Monohydrate | 5 g |
| Adjust pH to 10.20 | |
| Water to make | 1 l |
| Bleach-Fixing Solution | |
| Ethylenediaminetetraacetic Acid | 2 g |
| Ferric Salt of Ethylenediaminetetraacetate | 40 g |
| Sodium Sulfite | 5 g |
| Ammonium Thiosulfate | 70 g |
| Water to make | 1 l |

The thus-obtained color print showed an excellent color-reproducing ability with distinct colors. The cyan dye image had an absorption maximum at 673 mμ.

When this color print was irradiated for 20 days under the condition of 30,000 luxes in illuminance using a white fluorescent lamp, a density reduction of 0.03 was observed in the area where initial reflection density of the cyan dye image was 1.0. When it was left for 10 days under the high temperature and high humidity conditions of 60° C. and 75% in relative humidity, a density reduction of 0.05 was observed in the area where initial reflection density was 1.0. Thus, it showed a good color image stability.

Also, when one unexposed coated sample was left for 3 days under the conditions of 40° C. and 80% RH and the other for the same days under the conditions of 25° C. and 60% RH and, after stepwise exposure for sensitometry, the two samples were simultaneously subjected to the abovedescribed processing steps, no changes were observed in photographic characteristics such as maximum density, fog, gamma, etc., in spite of being left to such severe conditions. Thus, the light-sensitive material was shown to be stable.

EXAMPLE 5

10 g of the foregoing Coupler (29), i.e., N-n-hexadecyl-N-cyanoethyl-1-hydroxy-4-($\beta$-hydroxy-$\gamma$-methoxycarbonylmethylthio)propyloxy-2-naphthamide, 10 ml of tris-n-hexyl phosphate, and 20 ml of ethyl acetate were heated to 50° C. to dissolve, and the resulting solution was added to 100 ml of an aqueous solution containing 0.5 g of sodium p-dodecylbenzenesulfonate and 10 g of gelatin, and stirred followed by vigorous mechanical stirring to thereby emulsify and disperse the coupler together with the solvent.

The whole of this emulsion dispersion was added to 186 g of a reversal silver bromoiodide emulsion (containing $8.37 \times 10^{31\ 2}$ mol Ag and 13.0 g gelatin) containing 3 mol% iodide, and 12 ml of a 4% aqueous solution of 2-hydroxy-4,6-dichloro-s-triazine sodium salt was added thereto as a hardener. Finally, the pH was adjusted to 7.0, and the thus-obtained emulsion was coated on a polyethylene terephthalate film base in a coated silver amount of 0.88 g/m².

This sample was stepwise exposed for sensitometry, and subjected to the following processing steps.

| Processing Step | Temperature (°C.) | Time (minutes) |
|---|---|---|
| 1. First development | 38 | 3 |
| 2. Washing with water | " | 1 |
| 3. Reversal | " | 2 |
| 4. Color development | " | 6 |
| 5. Control | " | 2 |
| 6. Bleaching | " | 6 |
| 7. Fixing | " | 4 |
| 8. Washing with water | " | 4 |
| 9. Stabilizing | " | 1 |
| 10. Drying | | |

Each of the processing solutions used had the following compositions.

| First Developer Solution | |
|---|---|
| Water | 800 ml |
| Sodium Tetrapolyphosphate | 2.0 g |
| Sodium Hydrogen Sulfite | 8.0 g |
| Sodium Sulfite | 37.0 g |
| 1-Phenyl-3-pyrazolidone | 0.35 g |
| Hydroquinone | 5.5 g |
| Sodium Carbonate Monohydrate | 28.0 g |
| Potassium Bromide | 1.5 g |
| Potassium Iodide | 13.0 mg |
| Sodium Thiocyanate | 1.4 g |
| Water to make | 1 liter |
| Reversal Solution | |
| Water | 800 ml |
| Hexasodium Nitrilo-N,N,N-trimethylene Phosphonic Acid | 3.0 g |
| Stannous Chloride Dihydrate | 1.0 g |
| Sodium Hydroxide | 8.0 g |
| Glacial Acetic Acid | 15.0 ml |
| Water to make | 1 liter |
| Color Developer Solution | |
| Water | 800 ml |
| Sodium Tetrapolyphosphate | 2.0 g |
| Benzyl Alcohol | 5.0 ml |
| Sodium Sulfite | 7.5 g |
| Trisodium Phosphate (12 hydrate) | 36.0 g |
| Potassium Bromide | 1.0 g |
| Potassium Iodide | 90.0 mg |
| Sodium Hydroxide | 3.0 g |
| Citrazic Acid | 1.5 g |
| 4-Amino-3-methyl-N-ethyl-N-($\beta$-hydroxyethyl)aniline Sesquisulfate Monohydrate | 11.0 g |
| Ethylenediamine | 3.0 g |
| Water to make | 1.0 liter |
| Controlling Solution | |
| Water | 800 ml |
| Glacial Acetic Acid | 5.0 ml |
| Sodium Hydroxide | 3.0 g |
| Dimethylaminoethaneisothiourea Dihydrochloride | 1.0 g |
| Water to make | 1 liter |
| Bleaching Solution | |
| Water | 800 ml |
| Sodium Ethylenediaminetetraacetate Dihydrate | 2.0 g |
| Ammonium Iron (III) Ethylenediaminetetraacetate Dihydrate | 120.0 g |
| Potassium Bromide | 100.0 g |
| Water to make | 1 liter |
| Fixing Solution | |
| Water | 800 ml |
| Ammonium Thiosulfate | 80.0 g |
| Sodium Sulfite | 5.0 g |
| Sodium Hydrogen Sulfite | 5.0 g |
| Water to make | 1 liter |
| Stabilizing Bath | |
| Water | 800 ml |
| Formalin (37%) | 5.0 ml |
| Fuji Drywell | 5.0 ml |
| Water to make | 1.0 liter |

The thus-obtained color reversal image had an absorption maximum at 687 m$\mu$, and showed good color formation.

Further, the same sample was left for three days under the conditions of 40° C. and 75 RH%, stepwise exposed for sensitometry, and subjected to the above-described processings for comparison. No change was observed in photographic characteristics such as $D_{max}$, fog, gamma, sensitivity, etc. Thus, the coupler was shown to have excellent stability.

EXAMPLE 6

A silver bromoiodide emulsion containing 4 mol% iodide was coated on a film in a coated silver amount of 120 $\mu$g/cm² and in a thickness of 4.0$\mu$, and stepwise exposed for sensitometry followed by development processing at 27° C. for 4 minutes using the following color developer. Subsequent processing steps of washing, bleaching, washing, fixing, and washing were conducted according to Example 1 to obtain a cyan color image.

| Color Developer | |
|---|---|
| Sodium Sulfite | 5 g |
| 4-Amino-3-methyl-N,N-diethylaniline | |

-continued

| Color Developer | |
|---|---|
| Hydrochloride | 0.6 g |
| Sodium Carbonate Monohydrate | 15 g |
| Potassium Bromide | 0.5 g |
| Potassium Iodide (0.1% aq. soln.) | 5 ml |
| Coupler (28), i.e., 2-acetamido-6-chloro-4-[β,γ-(dicarboxymethylthio)-propyloxy]-5-methylphenol | 1.3 g |
| Methanol | 20 ml |
| Sodium Hydroxide | 2 g |
| Water to make | 1,000 ml |

This image was distinct cyan color image having an absorption maximum at 672 mμ.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material containing a colorless photographic cyan color forming coupler having, in a position for coupling with an oxidation product of an aromatic primary amine developing agent, a coupling-off group represented by the formula (I):

—O—R—S—$R_1$         (I)

wherein R represents a substituted alkylene group containing from 1 to 18 carbon atoms or an unsubstituted or substituted alkenylene group, and said alkylene group or alkenylene group may be straight or branched chain; and $R_1$ represents a substituted or unsubstituted alkyl group, an alkenyl group, an aralkyl group, an aralkenyl group, a cycloalkyl group, or a heterocyclic group and said alkyl group, alkenyl group, aralkyl group and aralkenyl group may be straight chain or branched chain; and said heterocyclic group being connected with a thio group at the position of a carbon atom of the heterocyclic group.

2. A light-sensitive material as in claim 1, wherein said coupler is represented by the formula:

A(—O—R—S—$R_1$)$_m$         (IA)

wherein R and $R_1$ are defined as in claim 1; A represents a cyan color forming coupler residue containing a naphtholic or phenolic nucleus; and m represents a positive integer.

3. A light-sensitive material as in claim 2, wherein R represents a substituted alkylene group having from 1 to 18 carbon atoms or an unsubstituted or substituted alkenylene group having from 2 to 18 carbon atoms.

4. A light-sensitive material as in claim 2, wherein $R_1$ represents an alkyl group having from 1 to 18 carbon atoms, an alkenyl group having from 2 to 18 carbon atoms, an aralkyl group having from 7 to 18 carbon atoms, an aralkenyl group having from 8 to 18 carbon atoms, a cycloalkyl group, or a 5-membered or 6-membered heterocyclic group, wherein each of said groups may be substituted.

5. A light-sensitive material as in claim 2, wherein $R_1$ represents a straight chain or branched chain alkyl group substituted with a carboxy group, a hydroxy group or a sulfo group, and R represents a straight or branched chain alkylene group substituted with an alkylthio group of the formula —S—$R_{11}$, wherein $R_{11}$ has the same meaning as defined for $R_1$, or a hydroxy group.

6. A light-sensitive material as in claim 2, wherein m is 1 or 2.

7. A light-sensitive material as in claim 2, 3, 4, 5 or 6 wherein A represents a cyan color forming coupler residue containing a naphtholic nucleus.

8. A light-sensitive material as in claim 2, 3, 4, 5 or 6 wherein A represents a cyan color forming coupler residue containing a phenolic nucleus.

9. A light-sensitive material as in claim 1, wherein said coupler is represented by the following general formulae (IIA) and (IIB)

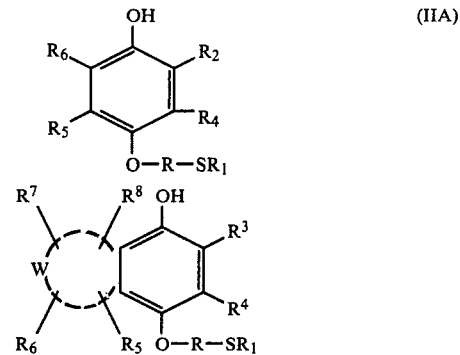

wherein R and $R_1$ each has the same meaning as defined in claim 1, $R_2$ represents a hydrogen atom, an aliphatic group containing up to 30 carbon atoms, an alkoxy group containing up to 30 carbon atoms, an aryloxy group, or a group represented by the following formulae:

—NH—CO—B     (III)

—NH—$SO_2$—B     (IV)

(V)

—NHCONH—B     (VI)

—CONH—B     (VII)

(VIII)

wherein B and B' may be the same or different and each represents an aliphatic group containing 1 to 32 carbon atoms, or an aryl group both of which may be substituted, D and D' each represents a B group are —OB, —NHB, and —$NB_2$, $R_3$ represents a hydrogen atom, an aliphatic group containing up to 30 carbon atoms, or a group represented by the above formula (VII) or (VIII), $R_4$, $R_5$, $R_6$, $R_7$ and $R_8$ each represents a hydrogen atom, a halogen atom, an alkyl group, an aryl group, an alkoxy group, an alkylthio group, a heterocyclic group, an amino group, a carbonamido group, a sulfonamido group, a sulfamyl group or a carbamyl group, W represents the non-metallic atoms necessary to complete a 5- or 6-membered carbacyclic or heterocyclic ring.

10. A light-sensitive material as in claim 1, wherein said coupler is represented by the formula (IIA)

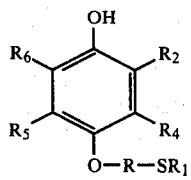
(IIA)

wherein R and R₁ each has the same meaning as defined in claim 1, $R_2$ represents a hydrogen atom, an aliphatic group containing up to 30 carbon atoms, an alkoxy group containing up to 30 carbon atoms, an aryloxy group, or a group represented by the following formulae

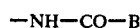   (III)

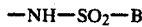   (IV)

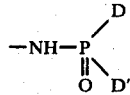   (V)

   (VI)

   (VII)

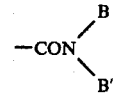   (VIII)

wherein B and B', both of which may be substituted, may be the same or different, and each represents an aliphatic group containing from 1 to 32 carbon atoms or an aryl group, D and D' each represents a B group or —OB, —NHB, and —NB₂; $R_4$, $R_5$ and $R_6$ each represents a hydrogen atom, a halogen atom, an alkyl group, an aryl group, an alkoxy group, an alkylthio group, a heterocyclic group, an amino group, a carbonamido group, a sulfoamido group, a sulfamyl group or a carbamyl group.

11. A light-sensitive material as in claim 1, wherein said coupler is represented by the formula (IIB)

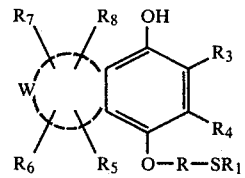
(IIB)

wherein R and R₁ each has the same meaning as defined in claim 1; $R_3$ represents a hydrogen atom, an aliphatic group containing up to 30 carbon atoms, or a group represented by the following formulae

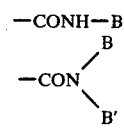   (VII) (VIII)

wherein B and B' both of which may be substituted, may be the same or different, and each represents an aliphatic group containing from 1 to 32 carbon atoms, or an aryl group; and $R_4$, $R_5$, $R_6$, $R_7$, and $R_8$ each represents a hydrogen atom, a halogen atom, an alkyl group, an aryl group, an alkoxy group, an alkylthio group, a heterocyclic group, an amino group, a carbonamido group, a sulfonamido group, a sulfamyl group, or a carbamyl group; and W represents the non-metallic atoms necessary to complete a 5- or 6-membered carboxyclic or heterocyclic ring.

12. A light-sensitive material as in claim 9, 10 or 11 wherein said coupler is diffusion resistant and contains a hydrophobic group having from 8 to 30 carbon atoms at at least one of the $R_1$–$R_8$ substituent positions.

13. A light-sensitive material of claim 1, 2, 9, 10 or 11 wherein said coupler is present in a silver halide emulsion layer.

14. A light-sensitive material as in claim 1, wherein said coupler is present in an amount of 1 to 1,500 g per mol of silver halide.

15. A light-sensitive material as in claim 1, wherein said coupler is present in a layer adjacent to a layer containing a p-substituted phenol derivative or in a layer containing a p-substituted phenol derivative.

16. A light-sensitive material as in claim 9 or 11, wherein W represents the non-metallic atoms necessary to complete a benzene ring.

17. A light-sensitive material as in claim 13, wherein said coupler is present in a red-sensitive silver halide emulsion layer.

18. A light-sensitive material as in claim 1, wherein R represents a substituted alkylene group containing from 1 to 4 carbon atoms.

* * * * *